United States Patent
Krainc et al.

(10) Patent No.: US 10,882,865 B2
(45) Date of Patent: Jan. 5, 2021

(54) PYRROLOPYRIMIDINE COMPOUNDS AND USES THEREOF FOR MODULATING GLUCOCEREBROSIDASE ACTIVITY

(71) Applicant: Northwestern University, Evanston, IL (US)

(72) Inventors: Dimitri Krainc, Chicago, IL (US); Richard B. Silverman, Winnetka, IL (US); Jianbin Zheng, Glencoe, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/555,827

(22) Filed: Aug. 29, 2019

(65) Prior Publication Data

US 2020/0071334 A1    Mar. 5, 2020

Related U.S. Application Data

(60) Provisional application No. 62/725,830, filed on Aug. 31, 2018.

(51) Int. Cl.
| | | |
|---|---|---|
| *C07D 487/04* | (2006.01) | |
| *C07D 513/04* | (2006.01) | |
| *A61K 31/517* | (2006.01) | |
| *A61K 31/519* | (2006.01) | |
| *A61P 25/16* | (2006.01) | |

(52) U.S. Cl.
CPC .................. *C07D 487/04* (2013.01)

(58) Field of Classification Search
CPC .. C07D 487/04; C07D 513/04; A61K 31/517; A61K 31/519; A61P 25/16
See application file for complete search history.

(56) References Cited

U.S. PATENT DOCUMENTS

| 9,802,942 B2 | 10/2017 | Krainc |
| 2017/0001976 A1 | 1/2017 | Krainc |
| 2017/0002013 A1 | 1/2017 | Krainc |
| 2017/0258870 A1 | 9/2017 | Schwake |
| 2018/0037586 A1 | 2/2018 | Krainc |
| 2018/0185368 A1* | 7/2018 | Skerlj ................. C07D 487/04 |
| 2018/0305367 A1 | 10/2018 | Krainc |
| 2019/0062303 A1 | 2/2019 | Krainc |
| 2019/0152980 A1 | 5/2019 | Krainc |

FOREIGN PATENT DOCUMENTS

| WO | 2012078855 A1 | 6/2012 |
| WO | 2019027765 A1 | 2/2019 |

OTHER PUBLICATIONS

Patnaik S et al., "Discovery, structure-activity relationship, and biological evaluation of noninhibitory small molecule chaperones of glucocerbrosidase," J. Med. Chem. Jun. 28, 2012;55(12):5734-48.

Zheng J et al. Design and Synthesis of Potent Quinazolines as Selective Beta-Glucocerebrosidase Modulators, J. Med. Chem. Sep. 22, 2016; 59(18): 8508-8520.

Zheng J et al., Beta-Glucocerebrosidase Modulators Promote Dimerization of Beta-Glucocerebrosidase and Reveal an Allosteric Binding Site, J. Am. Chem. Soc., 2018, 140 (18), pp. 5914-5924.

* cited by examiner

*Primary Examiner* — Bruck Kifle
(74) *Attorney, Agent, or Firm* — Quarles & Brady LLP

(57) ABSTRACT

Disclosed are new small molecules having a pyrrolopyrimidine core structure and the uses thereof for modulating glucocerebrosidase activity. Also disclosed are pharmaceutical compositions comprising the small molecules which may be administered in methods of treating diseases or disorders associated with glucocerebrosidase activity, including neurological diseases and disorders such as Gaucher's disease and Parkinson's disease. The small molecules may be utilized to generate activated glucocerebrosidase. The activated glucocerebrosidase thusly generated can be administered in enzyme replacement therapy and/or utilized in screening assays for new small molecules that bind to the activated glucocerebrosidase and/or modulate the activity of the activated glucocerebrosidase.

19 Claims, No Drawings

PYRROLOPYRIMIDINE COMPOUNDS AND USES THEREOF FOR MODULATING GLUCOCEREBROSIDASE ACTIVITY

CROSS-REFERENCE TO RELATED APPLICATIONS

This application claims priority to and the benefit of U.S. Patent Application No. 62/725,830, filed on Aug. 31, 2018, the entire contents of which are herein incorporated by reference.

FIELD

The field of the invention relates to new small molecules and uses of the new small molecules for modulating glucocerebrosidase (GCase) activity such as β-GCase activity. The new small molecules have a pyrrolopyrimidine core structure, such as a pyrrrolo[1,2-a]pyrimidine-8-carboxamide core structure, and the small molecules may be administered to treat diseases and disorders associated with aberrant glucocerebrosidase activity including, but not limited to neurodegenerative diseases, such as Gaucher's disease and Parkinson's disease.

BACKGROUND

Glucocerebrosidase (EC 3.2.1.45), which also is called β-glucocerebrosidase, (β-glucosidase, D-glucosyl-N-acyl-sphingosine glucohydrolase, or GCase, is an enzyme having glucosylceramidase activity. Glucocerebrosidase is required to cleave the beta-glucosidic linkage of the chemical glucocerebroside, which is an intermediate in glycolipid metabolism. Glucocerebrosidase is localized in the lysosome and disabling mutations in the gene for glucocerebrosidase (GBA1) are associated with abnormal accumulation of lipids in lysosomes including glucosylceramide (GL1).

Genetic diseases caused by mutations in GBA1 include neurodegenerative diseases such as Gaucher's disease and Parkinson's disease. Gaucher's disease is a rare genetic disease caused by GBA1 gene mutations. Currently, the treatment for Type 1 Gaucher's disease is enzyme replacement therapy (ERT) in which a modified form of glucocerebrosidase is administered intravenously every two weeks in order to reduce or prevent the buildup of lipids including GL1 in lysosomes. ERT is very expensive and not effective for neuronopathic forms of Gaucher's disease. Mutations in GBA1 also are linked to Parkinson's disease (PD) and are associated with an increased risk of PD.

SUMMARY

The present disclosure provides novel substituted pyrrolopyrimidine compounds which modulate glucocerebrosidase activity. The substituted pyrrolopyrimidine compounds disclosed herein have better chemical and physical properties than previous reported non-active site GCase inhibitors. (See Goldin et al., WO, "Substituted pyrazolopyrimidines as glucocerebrosidase activators." December 2010, WO2012078855; and Patnaik et al., "Discovery, structure-activity relationship, and biological evaluation of noninhibitory small molecule chaperones of glucocerbrosidase," J. Med. Chem. 2012 Jun. 28; 55(1`2):5734-48, the contents of which are incorporated herein by reference in their entireties). These better chemical and physical properties of the disclosed substituted pyrrolopyrimidine compounds include larger polar surface area, increased solubility, increased number of rotatable bonds, and increased number of potential hydrogen bonding members. The chemical and physical properties of the disclosed substituted pyrrolopyrimidine compounds also better meet the requirements for oral bioavailability and blood-brain penetration.

Some of the substituted pyrrolopyrimidine compounds in the present disclosure are capably of highly activating GCase. For example, some of the substituted pyrrolopyrimidine compounds bind to GCase covalently and activate wild-type GCase up to 70-100 fold. GCase thusly activated by the disclosed pyrrolopyrimidine compounds is observed to be more stable in an acidic environment than GCase that has not been activated. Therefore, when used in enzyme replacement therapy, the activated GCase likely can be administered at a lower dose and less frequently than GCase that has not been activated by the disclosed compounds.

The activated GCase disclosed herein also can be used in a GCase activity assay for screening compounds that bind and/or modulate the enzyme activity of GCase. The disclosed GCase activity assay is very useful to identify new compounds having a binding affinity and/or modulatory activity for GCase. No high throughput screening method has previously been developed based on such a binding affinity assay for activated GCase.

Some embodiments of the present disclosure provide new, small molecules having a substituted pyrrolopyryimidine core structure, in particular, a 4-methylpyrrrolo[1,2-a]pyrimidine-8-carboxamide core structure. The new, small molecules may be utilized for modulating glucocerebrosidase activity. The new, small molecules preferably modulate glucocerebrosidase activity by binding to glucocerebrosidase, optionally covalently, and activating glucocerebrosidase. The new small molecules may be formulated as pharmaceutical compositions that comprise the small molecules or that comprise activated glucocerebrosidase conjugated to the small molecules, which compositions may be administered in methods of treating and/or preventing diseases or disorders associated with glucocerebrosidase activity, including neurological diseases and disorders such as Gaucher's disease and Parkinson's disease. The activated glucocerebrosidase also may be utilized in screening methods for test compounds to identify new compounds that bind to activated glucocerebrosidase and/or that modulate the activity of activated glucocerebrosidase.

In some embodiments, the present disclosure provides a compound or a salt or solvate thereof having a Formula I:

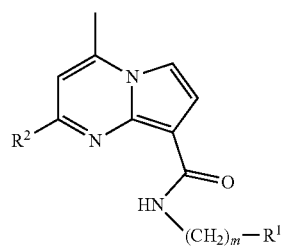

I wherein:
m is 0-6;
is selected from

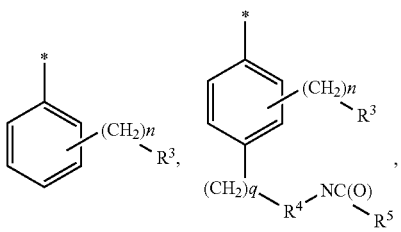

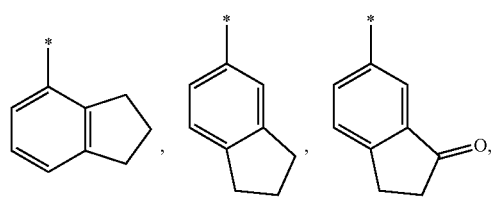

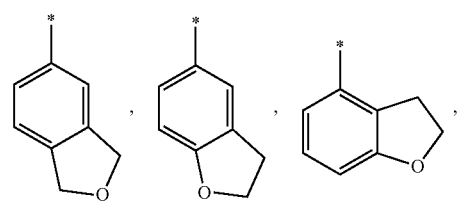

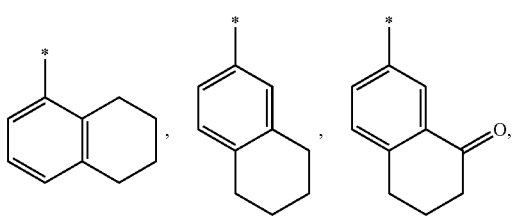

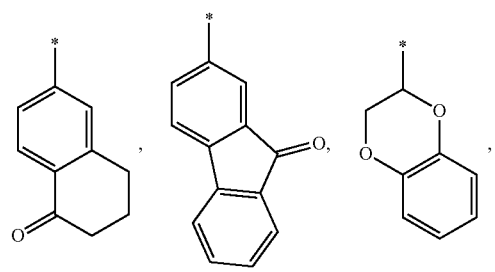

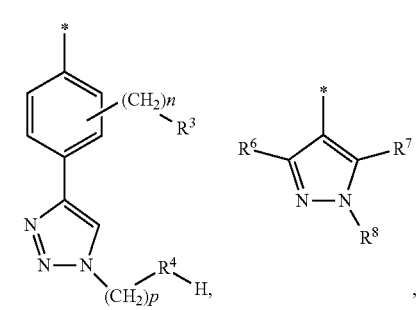

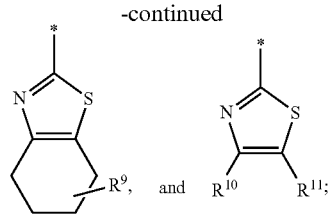

n is 0-6;
p is 0-6;
$R^2$ is C1-C6 alkyl or pyridinyl;
$R^3$ is selected from hydrogen, C1-C6 alkyl, C1-C6 alkoxy, phenyl, nitrophenyl, phenoxy, amino, —C(O)—O—$R^{12}$, —N—C(O)—$R^{13}$, and

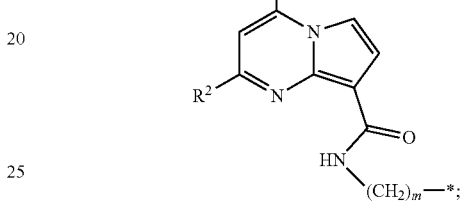

$R^4$ is —(OCH$_2$CH$_2$)$_q$— where q is 0-6;
$R^5$ is hydrogen, C1-C6 alkyl, or C3-C6 cycloalkyl;
$R^6$ and $R^7$ are independent selected from hydrogen and C1-C6 alkyl;
$R^8$ is hydrogen, C1-C6 alkyl, phenyl, or benzyl;
$R^9$ is hydrogen, C1-C6 alkyl, or C1-C6 dialkyl;
$R^{10}$ and $R^{11}$ are independently selected from hydrogen, C1-C6 alkyl, phenyl, and benzyl;
$R^{12}$ is selected from hydrogen, C1-C6 alkyl, phenyl, and N-succinimidyl; and
$R^{13}$ is selected from hydrogen, C1-C6 alkyl, C1-C6 (halo)alkyl, and C2-C6 alkenyl.

In further embodiments, the compound has a Formula Ia:

Ia

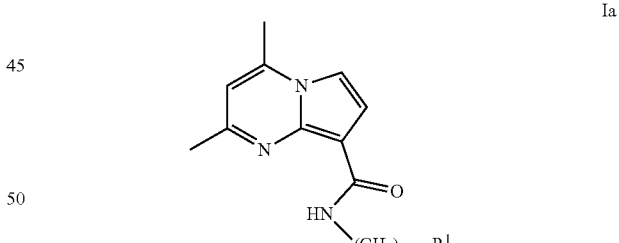

In some embodiments, the compound has a formula of:

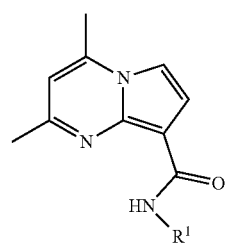

In further embodiments, the compound has a Formula Ib:

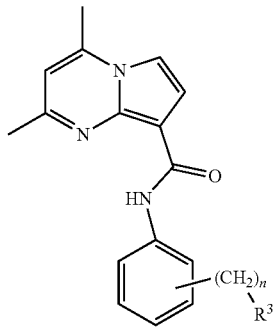

Ib

In some embodiments, the compound has a formula selected from:

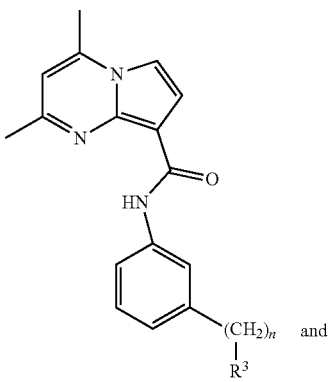

and

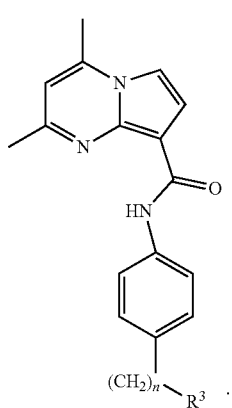

In further embodiments, R³ in any one of the preceding compounds is selected from —C(O)—O—R¹² and —N—C(O)—R¹³.

In some embodiments, the compound has a formula:

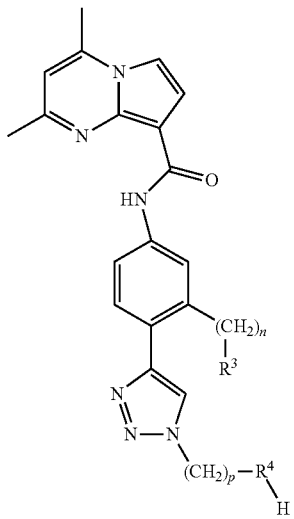

In further embodiments, the compound has a formula:

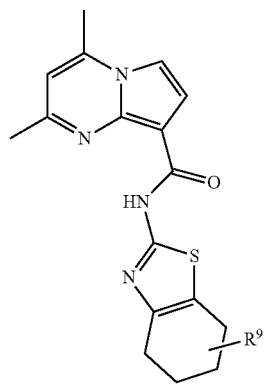

Some embodiments of the present disclosure provide a pharmaceutical composition comprising any one of the preceding compounds and a pharmaceutical carrier.

Further embodiments of the present disclosure provide a method for treating a disease or disorder that is associated with glucocerebrosidase activity in a subject in need thereof, the method comprising administering the pharmaceutical composition having any one of the preceding compounds and the pharmaceutical carrier.

In some embodiments, the disease or disorder is a neurological disease or disorder. In further embodiments, the degenerative neurological disease or disorder is Gaucher's disease. In some embodiments, the degenerative neurological disease or disorder is Parkinson's disease.

In further embodiments, any one of the preceding compounds is covalently attached to glucocerebrosidase to form a conjugate. The conjugate thus formed may be formulated as a pharmaceutical composition which optionally is administered to a subject in need thereof Some embodiments of the present disclosure provide a method of screening for a test compound having binding activity or modulatory activity for glucocerebrosidase, the method comprising: (a) contacting the test compound with an activated glucocerebrosidase that has been activated by covalently attaching to the glucocerebrosidase a compound according to any of the preceding formulas, and (b) detecting enzyme activity of the activated glucocerebrosidase in the presence of the test compound.

In further embodiments, detecting enzyme activity comprises (i) contacting the activated glucocerebrosidase and the test compound with a substrate that is metabolized by the activated glucocerebrosidase to generate a fluorescent metabolite; and (ii) detecting fluorescence of the fluorescent metabolite.

DETAILED DESCRIPTION

The disclosed subject matter further may be described utilizing terms as defined below.

Unless otherwise specified or indicated by context, the terms "a", "an", and "the" mean "one or more." For example, "a modulator of glucocerebrosidase activity" should be interpreted to mean "one or more modulators of glucocerebrosidase activity."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

The terms "subject," "patient," and "individual" may be used interchangeably herein. A subject may be a human subject. A subject may refer to a human subject having or at risk for acquiring a disease or disorder that is associated with aberrant glucocerebrosidase activity. As used herein, the term "aberrant" means higher or lower activity relative to a normal healthy subject. In specific embodiments, a subject exhibiting aberrant glucocerebrosidase may have or be at risk for acquiring Gaucher's disease and/or neurological diseases and disorders such as genetic and sporadic synucleinopathies, including Parkinson's disease, dementia with Lewy bodies, and multiple system atrophy associated with aberrant glucocerebrosidase activity.

As used herein, the term "modulate" means decreasing or inhibiting activity and/or increasing or augmenting activity. For example, modulating glucocerebrosidase activity may mean increasing or augmenting glucocerebrosidase activity and/or decreasing or inhibiting glucocerebrosidase activity. The compounds disclosed herein may be administered to modulate glucocerebrosidase activity for example, as a chaperone or activator.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

New Chemical Entities

New chemical entities and uses for chemical entities are disclosed herein. The chemical entities may be described using terminology known in the art and further discussed below.

As used herein, an asterick "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group (e.g., —$(CH_2)_n$— where n is an integer such as an integer between 1 and 20). An exemplary alkylene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number of ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^1$C(O)N(R$^2$)R$^3$, —C(O)NR$^2$R$^3$, or —C(O)NH$_2$, wherein R$^1$, R$^2$ and R$^3$, for example, are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Pyrrolopyrimidine Compounds

The compounds disclosed herein may be referred to as pyrrolopyrimidine compounds. In particular, the compounds disclosed herein by be referred to as pyrrolo[1,2-a]pyrimidine compounds. The disclosed compounds may include one or more substituents at one or more positions of the pyrrolo[1,2-a]pyrimidine core of the compound. In some embodiments, the pyrrolo[1,2-a]pyrimidine compounds disclosed herein may be referred to as "4-methylpyrrrolo[1,2-a]pyrimidine-8-carboxamide compounds."

The compounds or salt or solvates thereof may be described as having a Formula I as follows:

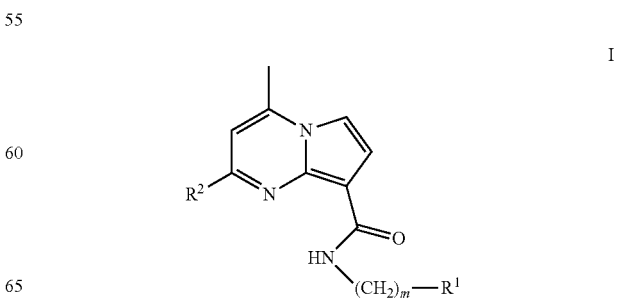

wherein:

m is 0-1, -2, -3, -4, -5, or -6;

$R^1$ is selected from

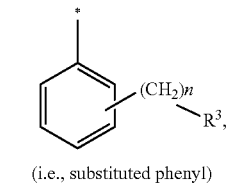
(i.e., substituted phenyl)

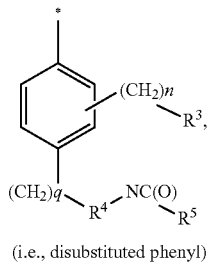
(i.e., disubstituted phenyl)

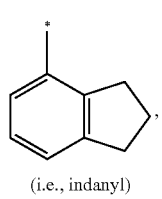
(i.e., indanyl)

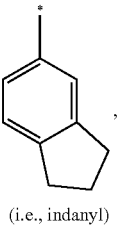
(i.e., indanyl)

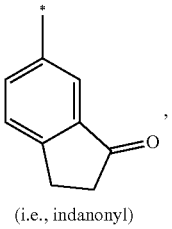
(i.e., indanonyl)

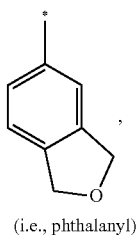
(i.e., phthalanyl)

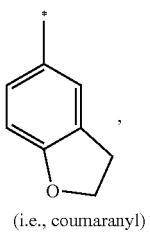
(i.e., coumaranyl)

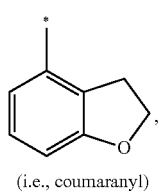
(i.e., coumaranyl)

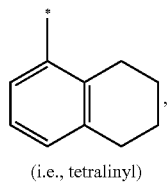
(i.e., tetralinyl)

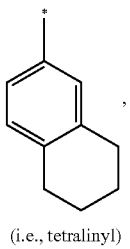
(i.e., tetralinyl)

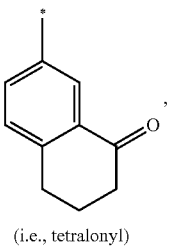
(i.e., tetralonyl)

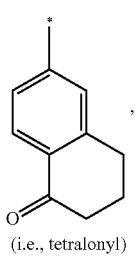
(i.e., tetralonyl)

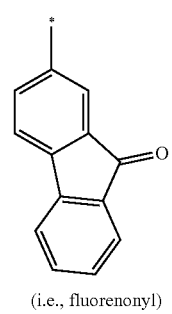
(i.e., fluorenonyl)

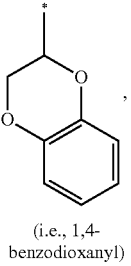
(i.e., 1,4-benzodioxanyl)

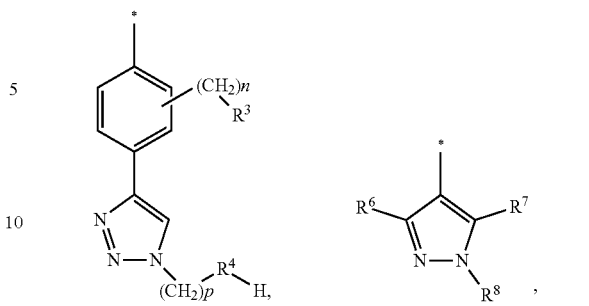

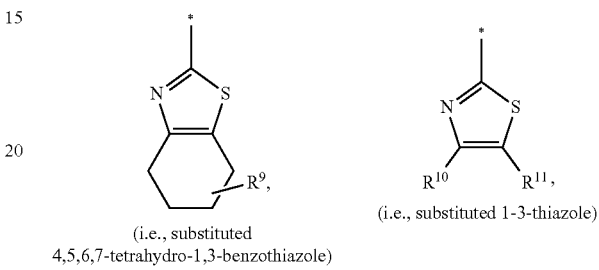
(i.e., substituted pyrazole)

(i.e., substituted 4,5,6,7-tetrahydro-1,3-benzothiazole)

(i.e., substituted 1-3-thiazole)

n is 0-1, -2, -3, -4, -5, or -6;

p is 0-1, -2, -3, -4, -5, or -6;

$R^2$ is C1-C6 alkyl or pyridinyl (e.g., pyridin-2-yl, pyridin-3-yl, or pyridin-4-yl);

$R^3$ is selected from hydrogen, C1-C6 alkyl, C1-C6 alkoxy, phenyl, nitrophenyl (e.g., 4-nitrophenyl), phenoxy, amino, *—C(O)—O—$R^{12}$, *—N—C(O)—$R^{13}$, and

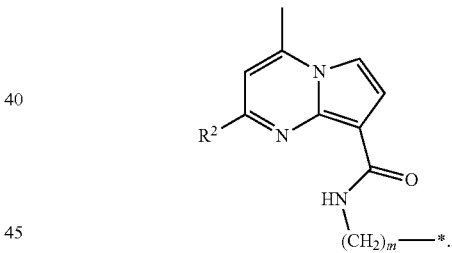

$R^4$ is —(OCH$_2$CH$_2$)$_q$— where q is 0-1, -2, -3, -4, -5, or -6;

$R^5$ is hydrogen, C1-C6 alkyl, or C3-C6 cycloalkyl;

$R^6$ and $R^7$ are independent selected from hydrogen and C1-C6 alkyl;

$R^8$ is hydrogen, C1-C6 alkyl, phenyl, or benzyl;

$R^9$ is hydrogen, C1-C6 alkyl (e.g., methyl), or C1-C6 dialkyl (e.g., dimethyl);

$R^{10}$ and $R^{11}$ are independently selected from hydrogen, C1-C6 alkyl (e.g., isobutyl), phenyl, and benzyl;

$R^{12}$ is selected from hydrogen, C1-C6 alkyl, phenyl, and N-succinimidyl; and $R^{13}$ is selected from hydrogen, C1-C6 alkyl, C1-C6 (halo) alkyl, and C2-C6 alkenyl.

In some embodiments, the pyrrolo[1,2-a]pyrimidine compounds disclosed herein may be referred to as "2,4-dimethylpyrrrolo[1,2-a]pyrimidine-8-carboxamide compounds," having a Formula Ia as follows:

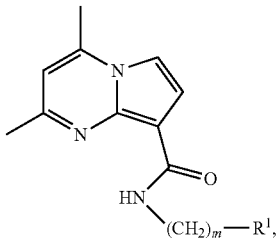

where R¹ is as defined above for Formula I.

The disclosed compounds may include two substituted 4-methylpyrrrolo[1,2-a]pyrimidine-8-carboxamide groups conjugated via a linker. Compounds that include two substituted 4-methylpyrrrolo[1,2-a]pyrimidine-8-carboxamide groups conjugated via a linker between the carboxamide groups may be illustrated as follows:

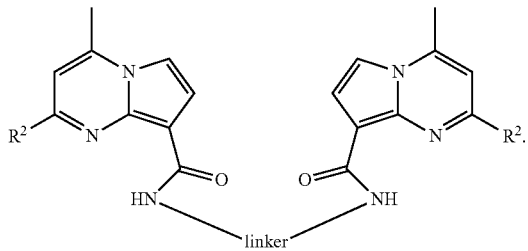

In some embodiments, the disclosed compounds having two substituted 4-methylpyrrrolo[1,2-a]pyrimidine-8-carboxamide groups conjugated via a linker optionally where the linker has a formula —(CH$_2$)$_v$-phenyl-(CH$_2$)$_w$— and v and w are independently selected from 0-1, 0-2, 0-3, 0-4, 0-5, or 0-6. In particular, the disclosed compounds having two substituted 4-methylpyrrrolo[1,2-a]pyrimidine-8-carboxamide groups conjugated via a linker may be described as having a formula as follows:

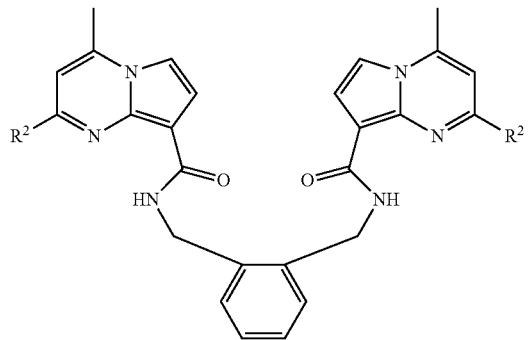

As noted, the compounds disclosed herein, including the substituted pyrimidine and fused pyrimidine compounds discussed above may have several chiral centers, and stereoisomers, epimers, and enantiomers are contemplated. The compounds may be optically pure with respect to one or more chiral centers (e.g., some or all of the chiral centers may be completely in the S configuration; some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers, or analogs or derivatives thereof are contemplated herein (e.g., a composition comprising at least about 90%, 95%, 99% or 100% pure stereoisomer, epimer, or enantiomer.) As used herein, formulae which do not specify the orientation at one or more chiral centers are meant to encompass all orientations and mixtures thereof.

The disclosed compounds may comprise or may be conjugated to a fluorophore. For example, the disclosed compounds may be conjugated to fluorophore via a linker (i.e., compound-linker-fluorophore). Suitable linkers may include but are not limited to a linker having a formula —NH—C(O)—(CH$_2$)$_p$—NH—C(O)—(CH$_2$CH$_2$O)$_q$—CH$_2$—CH$_2$—NH—C(O)— where p and q are independently selected from 1-18, 1-12, or 1-6 (e.g., where p=5 and q=4)). In some embodiments of the disclosed compounds of Formula I or Ia, any of substituents R¹, R², R³, R⁴, R⁵, R⁶, R⁷, R⁸, R⁹, R¹⁰, R¹¹, R¹², and R¹³, may comprise a fluorophore and/or may be conjugated to a fluorophore optionally via a linker, including fluorophores suitable for use in fluorescence polarization assays.

As used herein, a "fluorophore" is a chemical group that can be excited (e.g., by light or a chemical reaction) to emit fluorescence. Some suitable fluorophores may be excited by light to emit phosphorescence. As used herein, a "dye" may include a fluorophore. The compounds described herein may be conjugated to a fluorophore selected from but not limited to: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue;

Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. As used herein, a "fluorophore" may include a salt of the fluorophore.

Glucocerebrosidase Activity Modulation

The compounds disclosed herein preferably modulate activity of glucocerebrosidase. Modulation may include inhibiting or decreasing glucocerebrosidase activity. Modulation also may include activating or increasing glucocerebrosidase activity. Glucocerebrosidase activity may be assessed utilizing methods known in the art and the methods disclosed herein, including the methods disclosed in the Examples provided herein. In some embodiments, the compounds decrease or increase glucocerebrosidase activity relative to a control (e.g., by at least about 10%, 20%, 30%, 40%, 50%, 60%, 70%, 80%, 90%, 100%, 200%, 300%, 400%, 500%, 600%, 700%, 800%, 900%, 1000% or more (or within a range bounded by any of these values)). In other embodiments, the compounds activate glucocerebrosidase greater than about 2-fold, 3-fold, 4-fold, 5-fold, 10-fold, 20-fold, 30-fold, 40-fold, 50-fold, 60-fold, 70-fold, 80-fold, 90-fold, or 100-fold, relative to a control. In other embodiments, the compounds activate glucocerebrosidase with a maximum activation ($E_{max}$) greater than about 100%, 200%, 300%, 400%, 500%, 600%, 700%, 800%, 900%, 1000%, 1100%, 1200%, 1300%, 1400%, or 1500% (or within a range bounded by any of these values). In other embodiments, an $AC_{50}$ value for the compound in regard to activation of glucocerebrosidase may be determined and preferably the compound has an $AC_{50}$ value of less than about 10 µM, 5 µM, or 1 µM, 0.5 µM, 0.1 µM, 0.05 µM, 0.01 µM, 0.005 µM, or 0.001 µM (or within a range bounded by any of these values).

Methods for measuring glucocerebrosidase activity are known in the art. (See, e.g., U.S. Publication No. 2017/0001976 and U.S. Publication No. 2017/0002013 and Zheng et al. "Design and Synthesis of Potent Quinazolines as Selective β-Glucocerebrosidase Modulators, J. Med. Chem. 2016 September 22; 59(18): 8508-8520; the contents of which are incorporated herein by reference in their entireties).

Pharmaceutical Compositions and Methods of Administration

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that modulates glucocerebrosidase activity may be administered as a single compound or in combination with another compound that modulates glucocerebrosidase activity or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated glucocerebrosidase activity. For example, the pharmaceutical compositions may be utilized to treat patients having or at risk for acquiring Gaucher's disease and neurological diseases and disorders such as genetic and sporadic synucleinopathies, including Parkinson's disease, dementia with Lewy bodies, and multiple system atrophy associated with aberrant glucocerebrosidase activity. Suitable patients include, for example mammals, such as humans and non-human primates (e.g., chimps) or other mammals (e.g., dogs, cats, horses, rats, and mice). Suitable human patients may include, for example, those who have previously been determined to be at risk of having or developing Gaucher's disease and neurological diseases and disorders such as genetic and sporadic synucleinopathies, including Parkinson's disease, dementia with Lewy bodies, and multiple system atrophy associated with aberrant glucocerebrosidase activity.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with glucocerebrosidase activity.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The compounds disclosed in the present application may function as activators of glucocerebrosidase. For example, a compound disclosed herein may be reacted with glucocerebrosidase to prepare an activated glucocerebrosidase that is covalent attached to the compound. The activated glucocerebrosidase thusly formed may be prepared as a pharmaceutical composition to treat and/or prevent a disease or disorder that is associated with glucocerebrosidase activity as in enzyme replacement therapy, which is known in the art.

The following list of formulations is illustrative. These illustrative formulations may be suitable for preparing pharmaceutical compositions that include the disclosed compounds as "active ingredients." The following list of formulations is illustrative and should not be interpreted as limiting the present disclosure or claims in any way:

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| Active Ingredient | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| Active Ingredient | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules, each containing 80 mg medicament, are made as follows:

| Active Ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| Active Ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| Active Ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |

| | |
|---|---|
| Color | q.v. |
| Purified water to total | 5 ml |

The medicament is passed through a No. 45 mesh U.S. sieve and mixed with the sodium carboxymethyl, cellulose and syrup to form a smooth paste. The benzoic acid solution, flavor, and color are diluted with some of the water and added with stirring. Sufficient water is then added to produce the required volume.

Formulation 8

An intravenous formulation containing 100 mg of medicament per 5 ml dose can be prepared as follows:

| | |
|---|---|
| Active Ingredient | 100 mg |
| Mannitol | 100 mg |
| 5 N Sodium hydroxide | 200 ml |
| Purified water to total | 5 ml |

Examples

The followings Examples are illustrative only and are not intended to limit the scope of the claimed subject matter.

Pyrrolopyrimidine Compounds as Glucocerebrosidase Modulators and Their Applications Technical Field The technical field relates to the development of a new series of pyrrolopyrimidine glucocerebrosidase (GCase) activators and a compound-activated form of GCase implicated in Gaucher's disease and Parkinson's disease, and the activated GCase for high throughput screening of compounds that modulate the activity of GCase.

Abstract

Gaucher's disease is a rare genetic disease caused by GBA1 (glucocerebrosidase) gene mutations. Currently, the treatment for Type 1 Gaucher's disease is enzyme replacement therapy (ERT) administered every two weeks. ERT is very expensive and not effective for neuropathic forms of Gaucher's disease. Mutations in GBA1 are also linked to Parkinson's disease (PD), increasing the risk of PD. The pharmacological chaperone strategy to activate GCase has been previously attempted, but, none of the compounds achieved success in clinical trials because they targeted the active site of GCase. In contrast, our novel pyrrolopyrimidine compounds produce high activity of GCase. In addition, covalent binding pyrrolopyrimidine compounds activated wild-type GCase up to 70-100 fold in efficiency. We also found that the active enzyme is more stable in acidic environment. Moreover, we found that the activated enzyme could be inhibited with the same site binding modulators, suggesting its utility in high throughput screening of novel GCase modulators.

Applications

Applications of the disclosed technology include, but are not limited to: (i) prevention or treatment of Gaucher's disease and neurodegenerative diseases characterized by neuronal degradation or damage, including but not limited to Parkinson's disease via activation of glucocerebrosidase (GCase); (ii) preparation of an activated GCase that can be used as a new form of enzyme replacement therapy, including but not limited to Gaucher's disease; (iii) new compounds for glucocerebrosidase activation in synucleinopathies; and (iv) preparation of an activated enzyme that can be used for applications including but not limited to high throughput screening, testing of the binding affinity of compounds for activated GCase.

Advantages

Advantages of the disclosed technology include, but are not limited to: (i) the disclosed pyrrolopyrimidine-based compounds have improved enzyme activity and binding affinity with GCase and have better chemical and physical properties (such as polar surface area, molecular weight, solubility, CLogP, number of rotatable bonds, and number of hydrogen bonds) over previous GCase activators, and these properties are closer to those required for oral bioavailability and blood-brain barrier penetration; (ii) the disclosed pyrrolopyrimidine compound-activated GCase is more active in vitro and stable in acidic buffer than wild type GCase, and therefore, when used for enzyme replacement therapy, the enzyme amount and frequency could be reduced; and (iii) the disclosed activated enzyme can be used in enzyme activity assay, which is a very easy and quick method to test the binding affinity of the compounds with GCase; and (iv) the disclosed enzyme activity assay is very useful to find out new compounds binding with GCase, where no high throughput screening method based on a binding affinity assay had previously been developed and disclosed in the art.

Brief Summary of the Technology

Here, we disclose a new class of chemical compounds (substituted pyrrolopyrimidines), which are activators of glucocerebrosidase (GCase). Such compounds could be used for both the study of this enzyme and potentially for development into drug candidates for treatment or prevention of Gaucher's disease and neurodegenerative disorders. A compound activated enzyme showed much more activity and stability and can be used for Gaucher's disease and neurodegenerative disorders. The activated enzyme can be used in an enzyme activity assay, which is a very easy and quick method to test the binding affinity of the compounds with GCase. Further details are provided in the attached report.

Related Publications

Ehud Goldin, Juan Jose Marugan, Omid Motabar, Samarjit Patnaik, Ellen Sidransky, Noel Southall, Wendy Westbrook. Substituted pyrazolopyrimidines as glucocerebrosidase activators. December 2010, WO2012078855 A1.

Patnaik S1, Zheng W, Choi J H, Motabar O, Southall N, Westbroek W, Lea W A, Velayati A, Goldin E, Sidransky E, Leister W, Marugan J J. Discovery, structure-activity relationship, and biological evaluation of noninhibitory small molecule chaperones of glucocerebrosidase. J Med Chem. 2012; 55(12): 5734-48.

Krainc D., Silverman R B., and Zheng, J. Substituted 4-Methyl-Pyrrolo[1,2-a]Pyrimidine-8-carboxamide compounds and uses thereof for modulating glucocerebrosidase activity, Oct. 31, 2017. U.S. Pat. No. 9,802,942.

Summary

Gaucher's disease is a rare genetic disease caused by GBA1 (glucocerebrosidase) gene mutations. Currently, the treatment for Type 1 Gaucher's disease is enzyme replacement therapy (ERT), administered every two weeks. ERT is very expensive and not effective for neuropathic forms of Gaucher's disease. Mutations in GBA1 are also linked to Parkinson's disease (PD), increasing the risk of PD. The pharmacological chaperone strategy to activate GCase has been previously attempted, but, none of the compounds achieved success in clinical trials because they targeted the active site of GCase. In contrast, our novel pyrrolopyrimidine compounds produced high activity of GCase. In addition, covalent binding pyrrolopyrimidine compounds activated wild-type GCase up to 70-100 fold in efficiency. We also found that the active enzyme is more stable in an acidic environment, like the lysosome. Moreover, we found that the activated enzyme activity could be inhibited by competitive modulators in an enzyme activity assay, suggesting their utility in high throughput screening of novel GCase modulators.

Experimental

The disclosed pyrrolopyrimidine compounds were synthesized and tested using the methods described below. Additional methods for synthesizing and testing pyrrolopyrimidine compounds are described in the art. (See, e.g., Zheng et al., β-Glucocerebrosidase Modulators Promote Dimerization of β-Glucocerebrosidase and Reveal an Allosteric Binding Site, *J. Am. Chem. Soc.,* 2018, 140 (18), pp 5914-5924; and U.S. Pat. No. 9,802,942; the contents of which are incorporated herein by reference in their entireties).

Preparation of 2,5-dioxopyrrolidin-1-yl 2-(3-(2,4-dimethylpyrrolo[1,2-a]pyrimidine-8-carboxamido)phenyl)acetate (3)

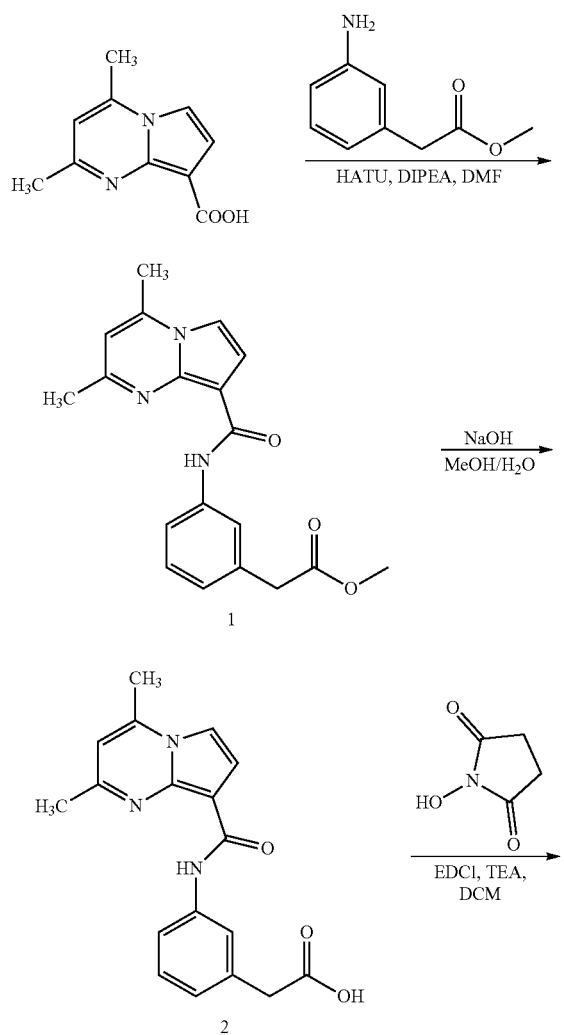

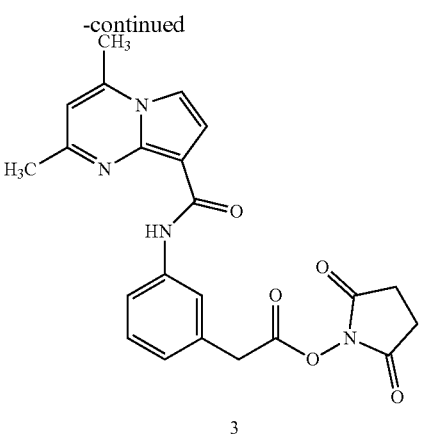

Preparation of methyl 2-(3-(2,4-dimethylpyrrolo[1,2-a]pyrimidine-8-carboxamido)phenyl)acetate (1). 2,4-Dimethylpyrrolo[1,2-a]pyrimidine-8-carboxylic acid (95 mg, 0.5 mmol), HATU (190 mg, 0.5 mmol), and diisopropylethylamine (350 µL) were dissolved in DMF (3 mL), and stirred for 30 min at room temperature. Methyl 2-(3-aminophenyl) acetate (83 mg, 0.5 mmol) was added into the reaction mixture. The mixture was allowed to stirred at 50° C. for 5 h. The mixture was cooled to room temperature, and diluted with water and filtered. The residue was washed with water (×2) and dried under vacuum to obtain a yellow solid (147 mg, 70%).

Preparation of 2-(3-(2,4-dimethylpyrrolo[1,2-a]pyrimidine-8-carboxamido)phenyl)acetic acid (2). To a solution of 4N NaOH (4 mL) and MeOH (4 mL) was added methyl 2-(3-(2,4-dimethylpyrrolo[1,2-a]pyrimidine-8-carboxamido)phenyl)acetate (1) (100 mg, 0.3 mmol), and the mixture was stirred at 50° C. overnight. The mixture was cooled to room temperature, and adjusted with 1N HCl to pH 1. The formed solid was filtered, washed with water (×2), and dried under vacuum to obtain a yellow solid (79 mg, 82%).

Preparation of 2,5-dioxopyrrolidin-1-yl 2-(3-(2,4-dimethylpyrrolo[1,2-a]pyrimidine-8-carboxamido)phenyl)acetate (3). A mixture of 2-(3-(2,4-dimethylpyrrolo[1,2-a]pyrimidine-8-carboxamido)phenyl)acetic acid (2) (31 mg, 0.1 mmol), N-Hydroxysuccinimide (11.5 mg, 0.1 mmol), EDCI (19 mg, 0.1 mmol), and triethylamine (15 µL) in DCM (2 mL) was stirred at 50° C. for 4 h. The mixture was diluted with DCM (20 mL), and washed with water (5 mL). The organic layer was washed with brine, dried ($Na_2SO_4$), concentrated. The residue was purified with flash chromatography to give yellow solid (25 mg, 60%).

$^1$H NMR (500 MHz, $CDCl_3$) δ 10.74 (s, 1H), 7.73 (d, J=9.0 Hz, 2H), 7.55 (d, J=3.2 Hz, 1H), 7.33 (t, J=7.8 Hz, 1H), 7.05 (d, J=3.5 Hz, 2H), 6.50 (s, 1H), 3.95 (s, 2H), 2.81 (s, 4H), 2.62 (s, 3H), 2.56 (s, 3H). $^{13}$C NMR (125 MHz, $CDCl_3$) δ 168.9, 166.7, 162.4, 155.5, 142.5, 140.0, 139.4, 131.9, 129.3, 123.6, 120.3, 118.9, 117.2, 108.3, 106.9, 105.7, 37.7, 25.5, 24.7, 18.1. HRMS (ESI): calcd for $C_{22}H_{21}N_4O_5$ $[M+H]^+$, 421.1506; found, 421.1506.

GCase Covalent Activation Assay with Compound 3. To wild-type GCase (22 µM, 1 mL, 1 equiv) in PBS (pH 7.4) was added covalent compound 3 in DMSO (0.89 mM, 50 µL, 2 equiv) in one portion and immediately vortexed for 5 sec. The reaction mixture was shaken at room temperature for 2 h, and another portion (25 µL, 1 equiv) of compound 3 was added, and reacted for 2 h. The reaction process was monitored by high resolution LC-MS Spectra. Then, the mixture was dialyzed by repeated buffer exchanges with 0.1 M acetic acid/sodium acetate buffer (pH 5.0) using Amicon Ultra 0.5 ml 10K centrifugal filters (Millipore). The concentrated enzyme was purified by size exclusion chromatography (Superdex 200 column, GE Healthcare Life Sciences), using 0.1 M acetic acid/sodium acetate buffer (pH 5.0) as the elution solvent. The purified enzyme was assayed with Res-β-Glc and 4MU-β-Glc substrates.

High Throughput Screen with Compound 6 Covalently Activated GCase. The compounds stock (10 mM) in DMSO solution (50 nL/well) were transferred to a black 384-well plate (25 μM). The compound 3 activated enzyme solution (10 μL, 2 nM final concentration) was transferred to the wells. After 5 min of incubation at room temperature, the enzyme reaction was initiated by the addition of blue substrate (4MU-β-Glc) (10 μL/well). The final concentration of the blue substrate was 1.5 mM. The blue substrate reaction was terminated by the addition of 10 μL/well stop solution (1 M NaOH and 1 M glycine mixture, pH 10) after 30 min of incubation at room temperature. The fluorescence was then measured in a Biotek Synergy H1 multi-mode plate reader with $\lambda_{ex}$=365 nm and $\lambda_{em}$=440 nm.

TABLE 1

Exemplary Compounds and Activities

| No. | Structures | $AC_{50}$ (μM) | Maximum Activation (Emax) (%) |
|---|---|---|---|
| 1 | 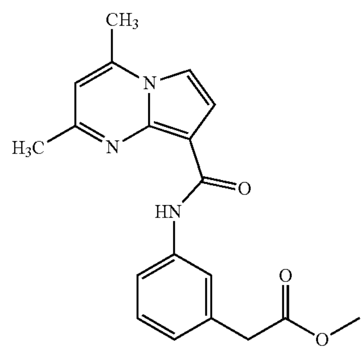 | 6.59 | 450 |
| 2 | 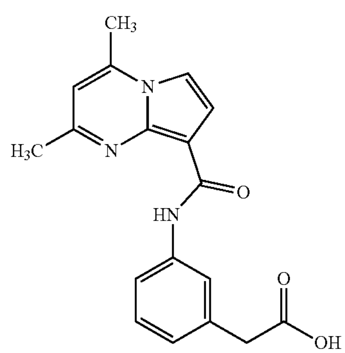 [SMILES: Cc1cc(C)n2ccc(C(=O)Nc3cccc(CC(=O)O)c3)c2n1] | 30 | 550 |
| 3 | 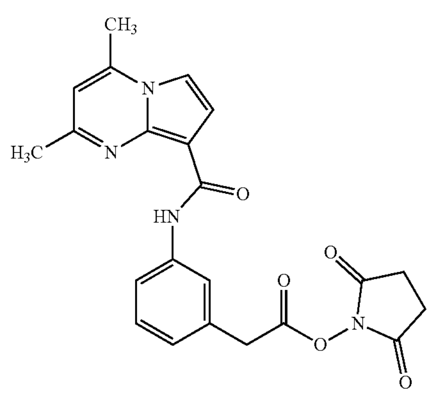 [SMILES: Cc1cc(C)n2ccc(C(=O)Nc3cccc(CC(=O)ON4C(=O)CCC4=O)c3)c2n1] | 9.09 | 500 |

TABLE 1-continued
Exemplary Compounds and Activities
| No. | Structures | AC$_{50}$ (μM) | Maximum Activation (Emax) (%) |
|---|---|---|---|
| 4 | 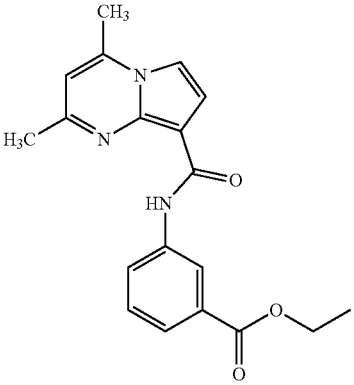 [SMILES: CCOC(=O)c1cccc(NC(=O)c2ccn3c(C)cc(C)nc23)c1] | 1.18 | 400 |
| 5 | 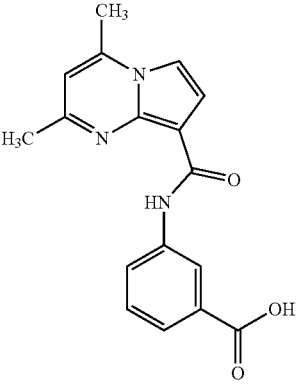 [SMILES: Cc1cc(C)n2ccc(C(=O)Nc3cccc(C(=O)O)c3)c2n1] | 2.87 | 175 |
| 6 | 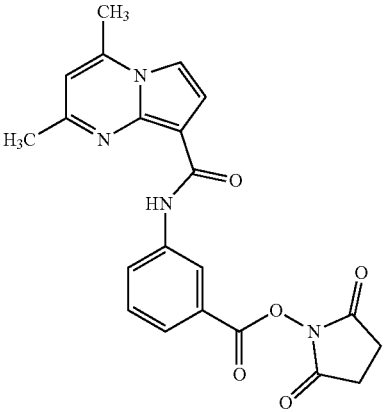 [SMILES: Cc1cc(C)n2ccc(C(=O)Nc3cccc(C(=O)ON4C(=O)CCC4=O)c3)c2n1] | 4.59 | 460 |

TABLE 1-continued

Exemplary Compounds and Activities

| No. | Structures | AC$_{50}$ (μM) | Maximum Activation (Emax) (%) |
|---|---|---|---|
| 7 | 2,4-dimethylpyrrolo[1,2-a]pyrimidine-8-carboxylic acid (3-aminophenyl)amide | 3.39 | 210 |
| 8 | 2,4-dimethylpyrrolo[1,2-a]pyrimidine-8-carboxylic acid [3-(2-chloroacetylamino)phenyl]amide | 3.43 | 480 |
| 9 | 2,4-dimethylpyrrolo[1,2-a]pyrimidine-8-carboxylic acid (3-isopropylphenyl)amide | 2.23 | 280 |
| 10 | 2,4-dimethylpyrrolo[1,2-a]pyrimidine-8-carboxylic acid (2,3-dihydro-1H-inden-4-yl)amide | 0.77 | 202 |

TABLE 1-continued

| | Exemplary Compounds and Activities | | |
|---|---|---|---|
| No. | Structures | $AC_{50}$ (μM) | Maximum Activation ($E_{max}$) (%) |
| 11 | | 1.41 | 400 |
| 12 | | 3.44 | 300 |
| 13 | | 0.63 | 180 |
| 14 | | 6.46 | 1100 |

TABLE 1-continued
Exemplary Compounds and Activities
| No. | Structures | AC$_{50}$ (μM) | Maximum Activation (Emax) (%) |
|---|---|---|---|
| 15 | 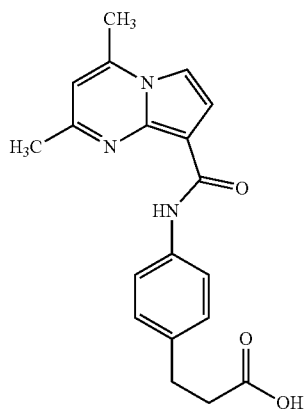 [SMILES: Cc1cc(C)n2ccc(C(=O)Nc3ccc(CCC(=O)O)cc3)c2n1] | 36.58 | 700 |
| 16 | 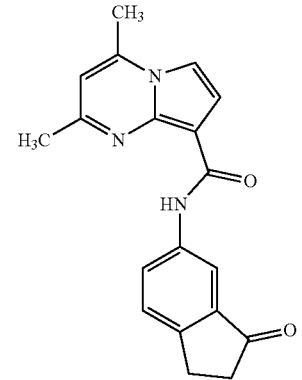 [SMILES: Cc1cc(C)n2ccc(C(=O)Nc3ccc4c(c3)C(=O)CC4)c2n1] | 1.49 | 225 |
| 17 | 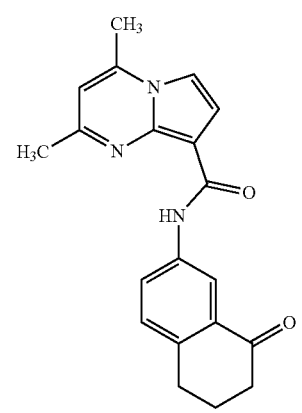 [SMILES: Cc1cc(C)n2ccc(C(=O)Nc3ccc4c(c3)C(=O)CCC4)c2n1] | 3.88 | 750 |

TABLE 1-continued

Exemplary Compounds and Activities

| No. | Structures | AC$_{50}$ (μM) | Maximum Activation (Emax) (%) |
|---|---|---|---|
| 18 | (structure) | NA | |
| 19 | (structure) | 0.71 | 250 |
| 20 | (structure) | 6.10 | 550 |

TABLE 1-continued

| | Exemplary Compounds and Activities | | |
|---|---|---|---|
| No. | Structures | $AC_{50}$ (μM) | Maximum Activation (Emax) (%) |
| 21 | [structure: 2,4-dimethylpyrrolo[1,2-a]pyrimidine-8-carboxamide linked via NH to 4-carboxyphenyl] | 35.48 | 622 |
| 22 | [structure: 2,4-dimethylpyrrolo[1,2-a]pyrimidine-8-carboxamide linked via NH to 4-(carboxymethyl)phenyl] | 35.48 | 429 |
| 23 | [structure: 2,4-dimethylpyrrolo[1,2-a]pyrimidine-8-carboxamide linked via NH-CH2 to 2,3-dihydro-1,4-benzodioxin-2-yl] | 28.2 | 644 |

TABLE 1-continued
Exemplary Compounds and Activities
| No. | Structures | AC$_{50}$ (μM) | Maximum Activation (Emax) (%) |
| --- | --- | --- | --- |
| 24 | 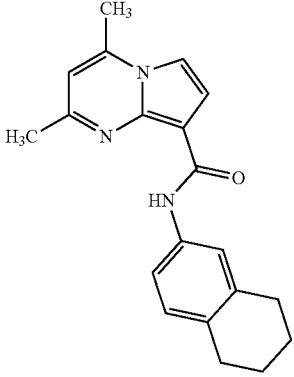 [SMILES: Cc1cc(C)n2ccc(C(=O)Nc3ccc4c(c3)CCCC4)c2n1] | 3.55 | 527 |
| 25 | 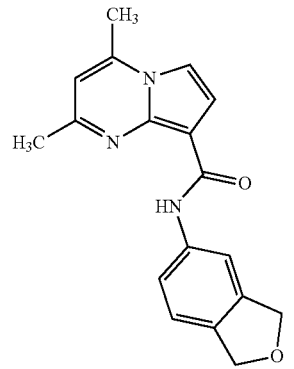 [SMILES: Cc1cc(C)n2ccc(C(=O)Nc3ccc4c(c3)COC4)c2n1] | 7.94 | 456 |
| 26 | 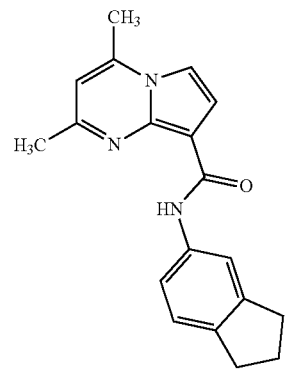 [SMILES: Cc1cc(C)n2ccc(C(=O)Nc3ccc4c(c3)CCC4)c2n1] | 1.12 | 290 |

TABLE 1-continued

Exemplary Compounds and Activities

| No. | Structures | AC$_{50}$ (μM) | Maximum Activation (Emax) (%) |
|---|---|---|---|
| 27 | 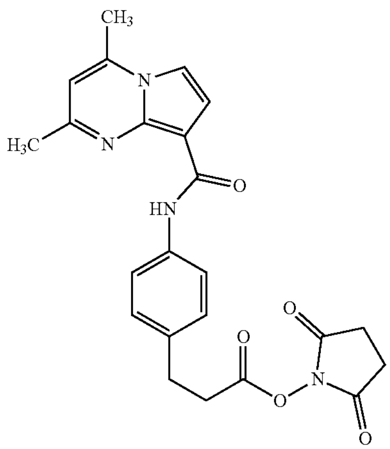 [SMILES: Cc1cc(C)n2ccc(C(=O)Nc3ccc(CCC(=O)ON4C(=O)CCC4=O)cc3)c2n1] | 2.82 | 620 |
| 28 | 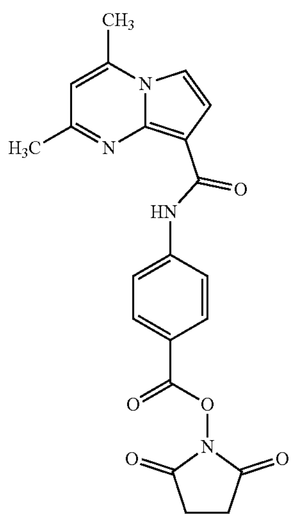 [SMILES: Cc1cc(C)n2ccc(C(=O)Nc3ccc(C(=O)ON4C(=O)CCC4=O)cc3)c2n1] | 50 | 115 |
| 29 | 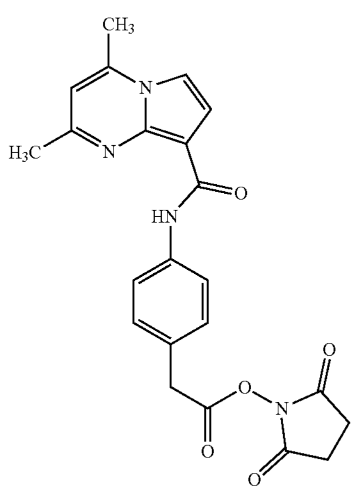 [SMILES: Cc1cc(C)n2ccc(C(=O)Nc3ccc(CC(=O)ON4C(=O)CCC4=O)cc3)c2n1] | 4.47 | 374 |

TABLE 1-continued

Exemplary Compounds and Activities

| No. | Structures | AC$_{50}$ (μM) | Maximum Activation (Emax) (%) |
|---|---|---|---|
| 30 | 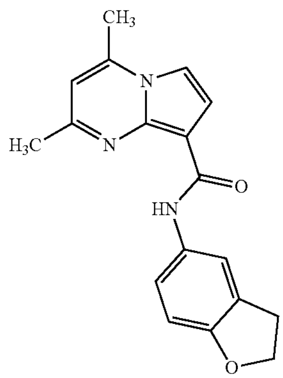 [SMILES: Cc1cc(C)n2ccc(C(=O)Nc3ccc4c(c3)CCO4)c2n1] | 1.12 | 198 |
| 31 | 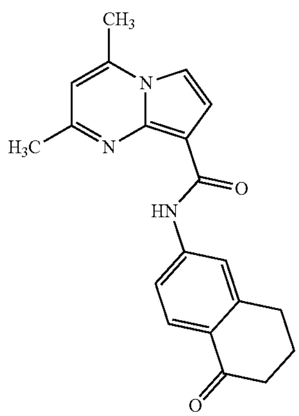 [SMILES: Cc1cc(C)n2ccc(C(=O)Nc3ccc4c(c3)CCCC4=O)c2n1] | 1.00 | 355 |
| 32 | 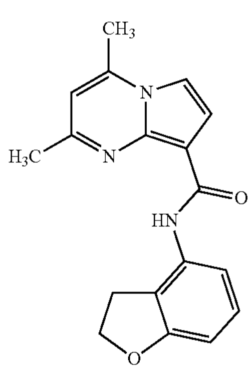 [SMILES: Cc1cc(C)n2ccc(C(=O)Nc3cccc4c3CCO4)c2n1] | NA | |

TABLE 1-continued
Exemplary Compounds and Activities
| No. | Structures | AC$_{50}$ (μM) | Maximum Activation (Emax) (%) |
|---|---|---|---|
| 33 | 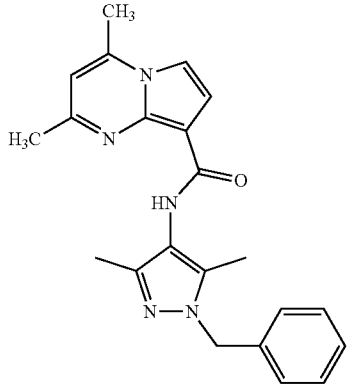 [SMILES: Cc1cc(C)n2ccc(C(=O)Nc3c(C)nn(Cc4ccccc4)c3C)c2n1] | 39.8 | 914 |
| 34 | 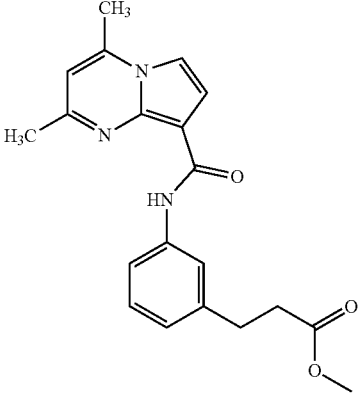 | 3.55 | 578 |
| 35 | 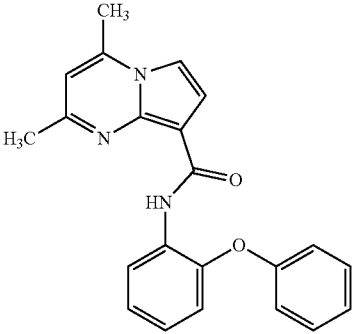 [SMILES: Cc1cc(C)n2ccc(C(=O)Nc3ccccc3Oc3ccccc3)c2n1] | 2.24 | 298 |
| 36 | 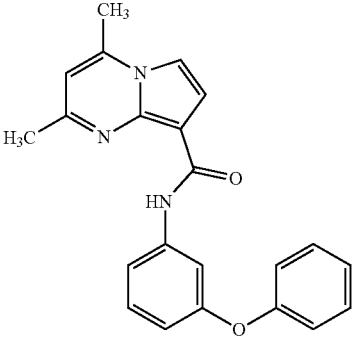 [SMILES: Cc1cc(C)n2ccc(C(=O)Nc3cccc(Oc4ccccc4)c3)c2n1] | 1.42 | 280 |

TABLE 1-continued

| | Exemplary Compounds and Activities | | |
|---|---|---|---|
| No. | Structures | $AC_{50}$ (μM) | Maximum Activation (Emax) (%) |
| 37 | | 8.91 | 427 |
| 38 | | 4.47 | 810 |
| 39 | | 10 | 1446 |

TABLE 1-continued

Exemplary Compounds and Activities

| No. | Structures | AC$_{50}$ (μM) | Maximum Activation (Emax) (%) |
|---|---|---|---|
| 40 | 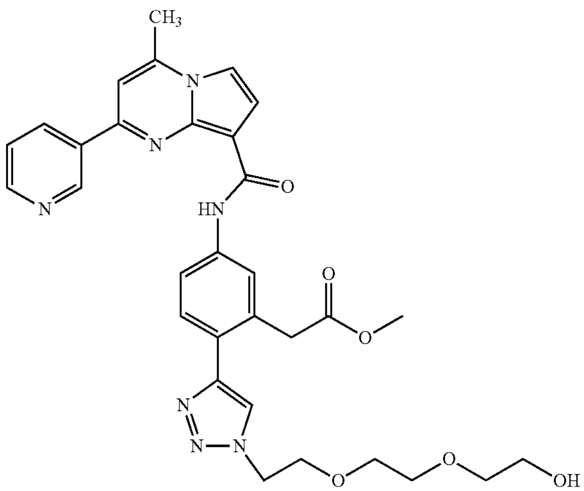 [SMILES: COC(=O)Cc1cc(NC(=O)c2ccn3c(C)cc(-c4cccnc4)nc23)ccc1-c1cn(CCOCCOCCO)nn1] | 4.47 | 1366 |
| 41 | 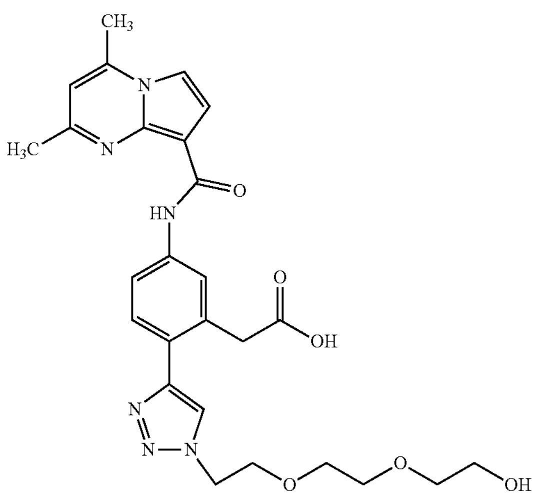 [SMILES: Cc1cc(C)n2ccc(C(=O)Nc3ccc(-c4cn(CCOCCOCCO)nn4)c(CC(=O)O)c3)c2n1] | 28.18 | 1187 |
| 42 | 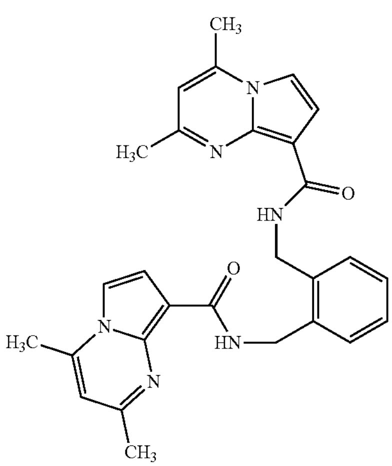 [SMILES: Cc1cc(C)n2ccc(C(=O)NCc3ccccc3CNC(=O)c3ccn4c(C)cc(C)nc34)c2n1] | 5.0 | 715 |

TABLE 1-continued

Exemplary Compounds and Activities

| No. | Structures | AC$_{50}$ (μM) | Maximum Activation (Emax) (%) |
| --- | --- | --- | --- |
| 43 | *4,7-dimethyl-N-(3-phenylphenyl)pyrrolo[1,2-a]pyrimidine-8-carboxamide* | 1.41 | 296 |
| 44 | *4,7-dimethyl-N-(4,5,6,7-tetrahydrobenzothiazol-2-yl)pyrrolo[1,2-a]pyrimidine-8-carboxamide* | 1.58 | 342 |
| 45 | *4,7-dimethyl-N-(6-methyl-4,5,6,7-tetrahydrobenzothiazol-2-yl)pyrrolo[1,2-a]pyrimidine-8-carboxamide* | 1.78 | 325 |

TABLE 1-continued

Exemplary Compounds and Activities

| No. | Structures | AC$_{50}$ (μM) | Maximum Activation (Emax) (%) |
|---|---|---|---|
| 46 | 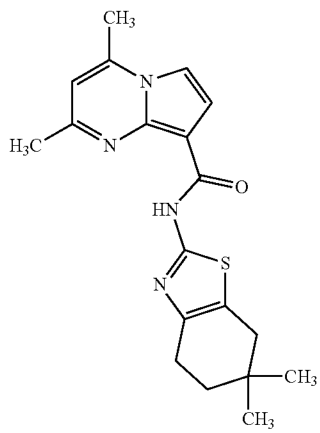 | 1.12 | 230 |
| 47 | 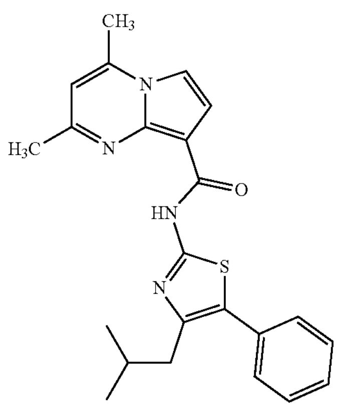 [SMILES: Cc1cc(C)n2ccc(C(=O)Nc3nc(CC(C)C)c(-c4ccccc4)s3)c2n1] | NA | |
| 48 | 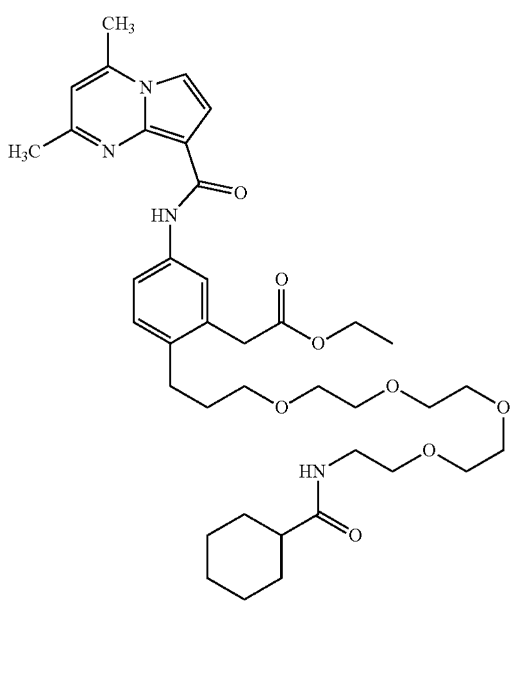 [SMILES: CCOC(=O)Cc1cc(NC(=O)c2ccn3c(C)cc(C)nc23)ccc1CCCOCCOCCOCCOCCNC(=O)C1CCCCC1] | 3.16 | 796 |

TABLE 1-continued

Exemplary Compounds and Activities

| No. | Structures | AC$_{50}$ (μM) | Maximum Activation (Emax) (%) |
|---|---|---|---|
| 49 | 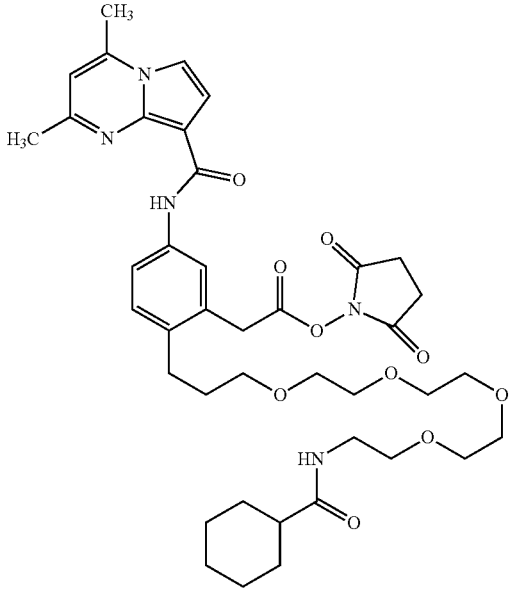 [SMILES: Cc1cc(C)n2ccc(C(=O)Nc3ccc(CCCOCCOCCOCCOCCNC(=O)C4CCCCC4)c(CC(=O)ON4C(=O)CCC4=O)c3)c2n1] | 3.55 | 1150 |
| 50 | 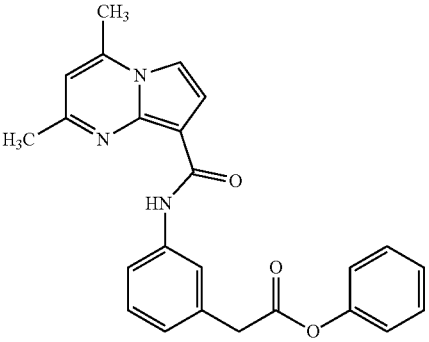 [SMILES: Cc1cc(C)n2ccc(C(=O)Nc3cccc(CC(=O)Oc4ccccc4)c3)c2n1] | 4.47 | 230 |
| 51 | 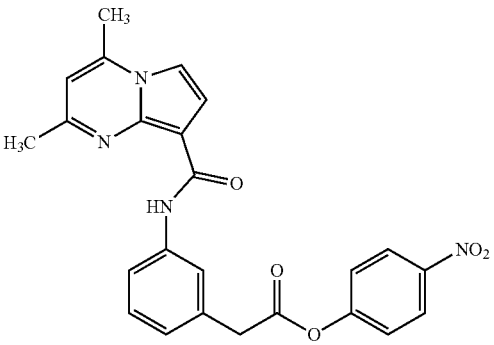 [SMILES: Cc1cc(C)n2ccc(C(=O)Nc3cccc(CC(=O)Oc4ccc([N+](=O)[O-])cc4)c3)c2n1] | 10 | 172 |

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound or a pharmaceutically acceptable salt thereof having a Formula I:

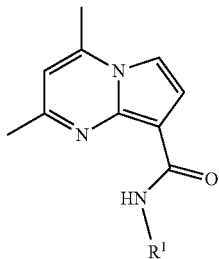

wherein:
R¹ is

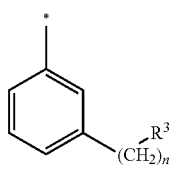

n is 0-6;
R³ is selected from C1-C6 alkyl, phenyl, phenoxy, amino, —C(O)—O—R¹², and —N—C(O)—R¹³;
R¹² is selected from hydrogen, C1-C6 alkyl, phenyl, nitrophenyl, and N-succinimidyl; and
R¹³ is selected from hydrogen, C1-C6 alkyl, C1-C6 (halo)alkyl, and C2-C6 alkenyl.

2. The compound of claim 1 having a formula selected from:

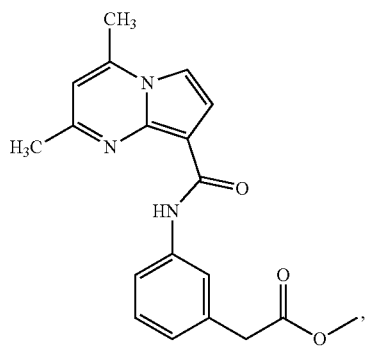

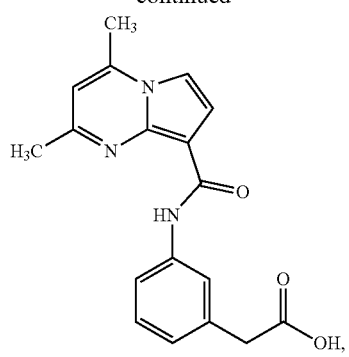

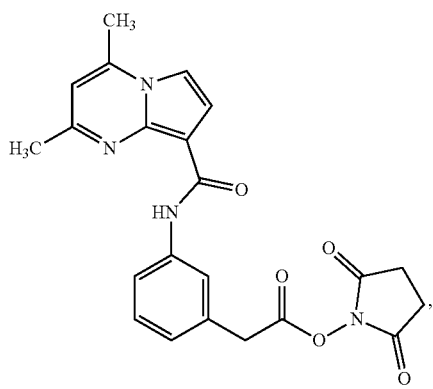

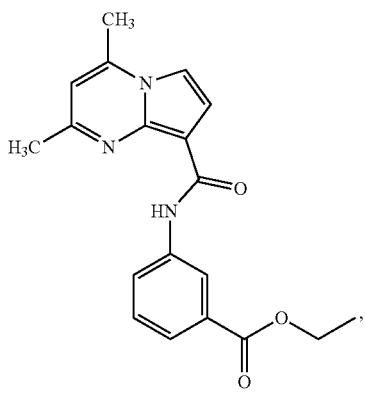

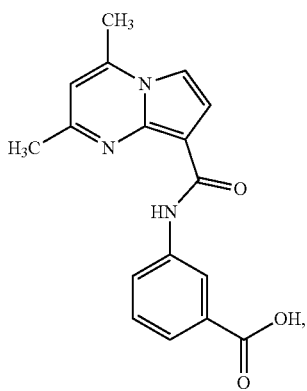

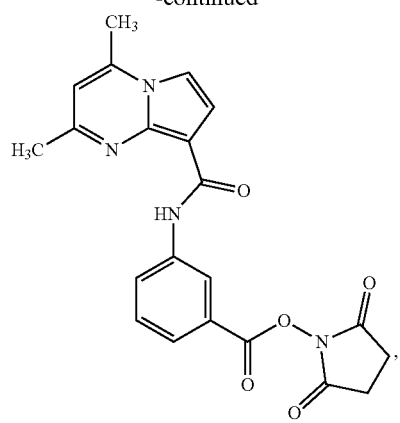
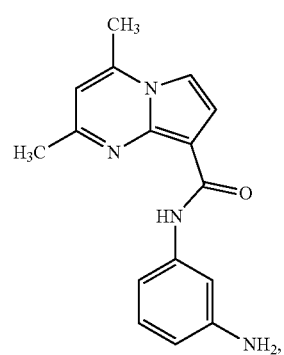
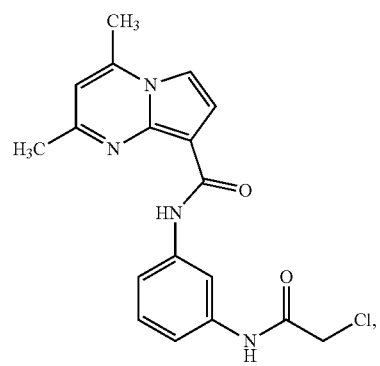
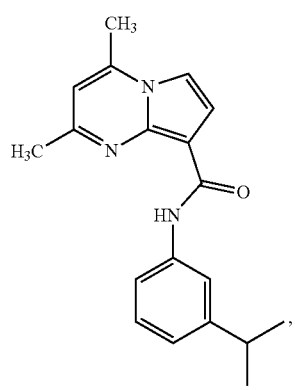
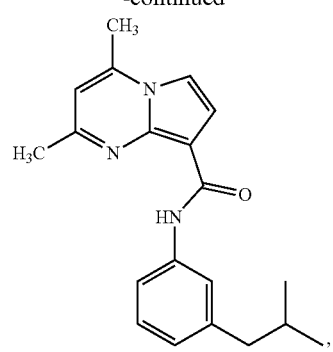
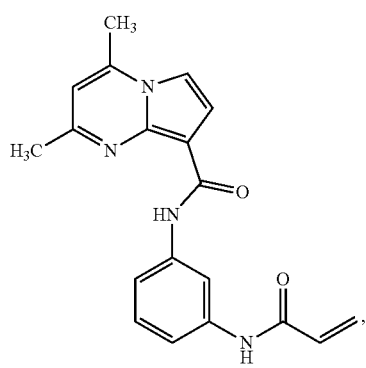
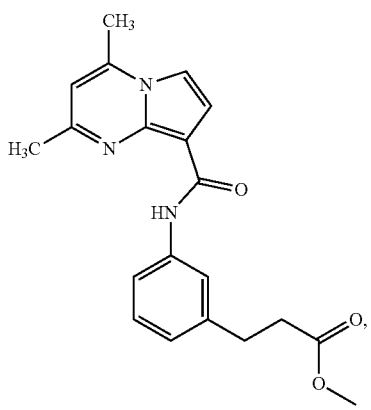
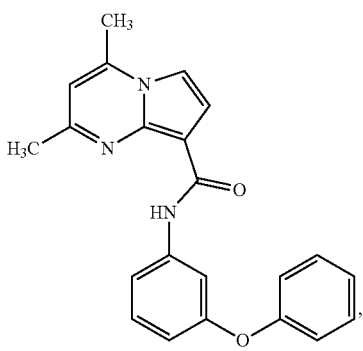

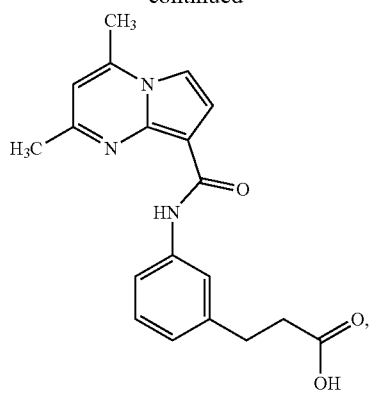

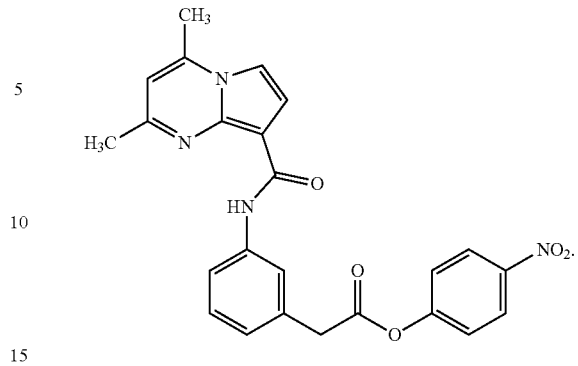

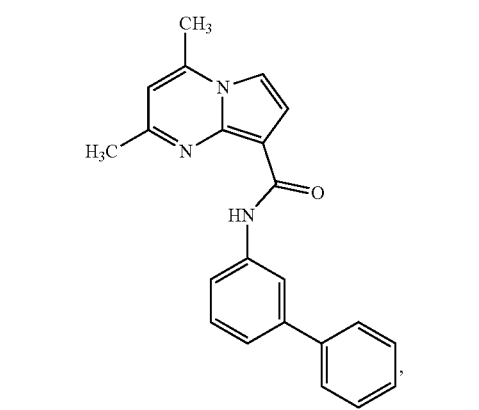

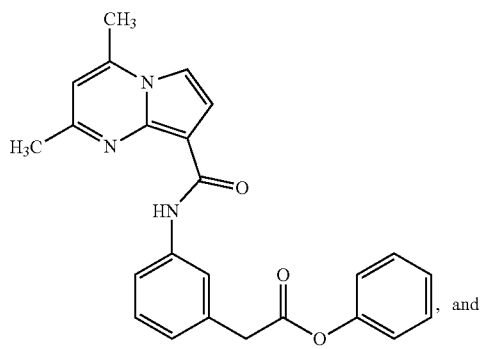

, and

3. A pharmaceutical composition comprising an effective amount of the compound of claim 1 and a pharmaceutical carrier.

4. A method for treating Gaucher's disease or Parkinson's disease in a subject in need thereof, the method comprising administering to the subject the composition of claim 3.

5. A conjugate comprising the compound of claim 1 covalently attached to glucocerebrosidase.

6. A pharmaceutical composition comprising: (i) an effective amount of the conjugate of claim 5; and (ii) a pharmaceutical carrier.

7. A method for treating Gaucher's disease or Parkinson's disease in a subject in need thereof, the method comprising administering to the subject the composition of claim 6.

8. A method of screening for a test compound having binding activity or modulatory activity for glucocerebrosidase, the method comprising: (a) contacting the test compound with an activated glucocerebrosidase that has been activated by covalently attaching to the glucocerebrosidase a compound according to claim 1 and (b) detecting enzyme activity of the activated glucocerebrosidase in the presence of the test compound.

9. The method of claim 8, wherein detecting enzyme activity comprises (i) contacting the activated glucocerebrosidase and the test compound with a substrate that is metabolized by the activated glucocerebrosidase to generate a fluorescent metabolite; and (ii) detecting fluorescence of the fluorescent metabolite.

10. A compound or a pharmaceutically acceptable salt thereof having a Formula I:

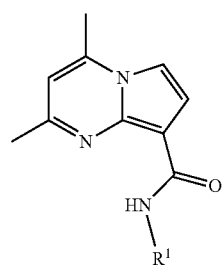

I wherein:
R¹ is
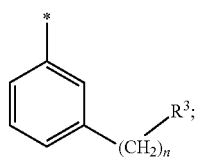
n is 0-6;
R³ is —C(O)—O—R¹²; and
R¹² is selected from hydrogen, C1-C6 alkyl, phenyl, nitrophenyl, and N-succinimidyl.
11. The compound of claim 10 having a formula selected from:
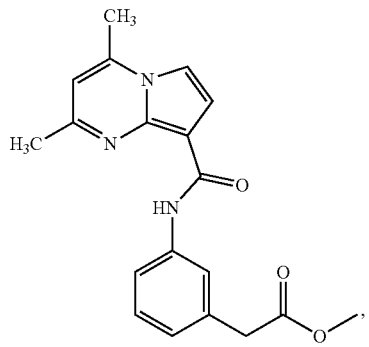
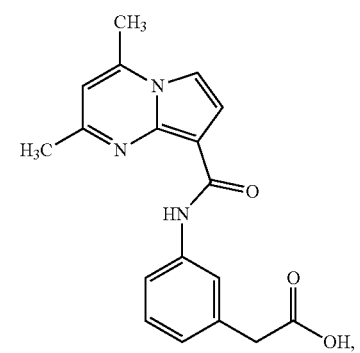
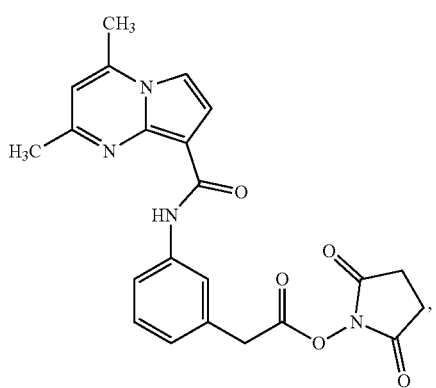
-continued
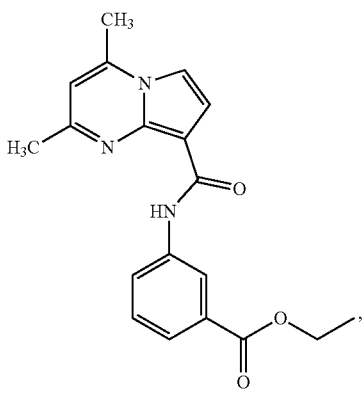
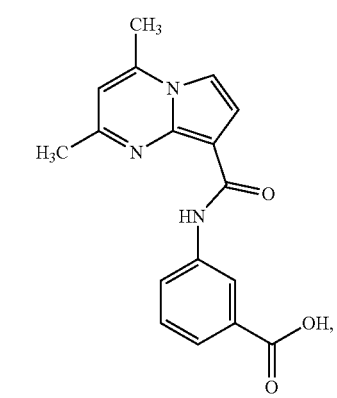
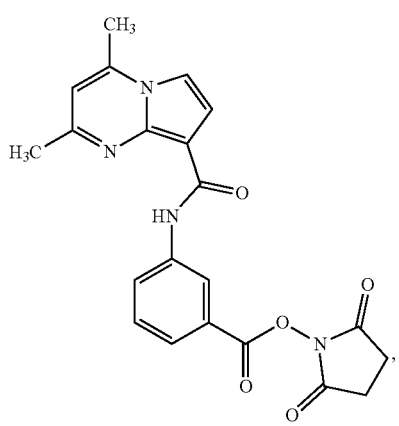
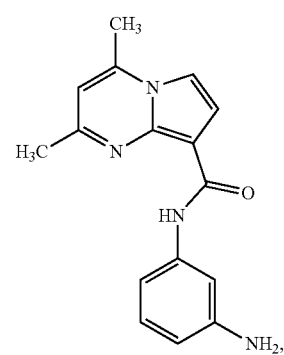

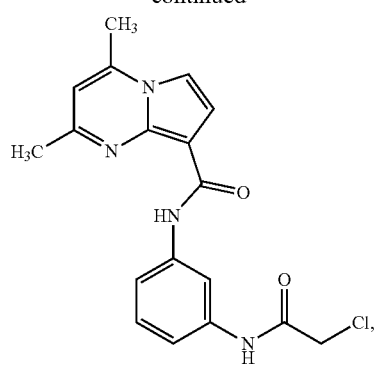
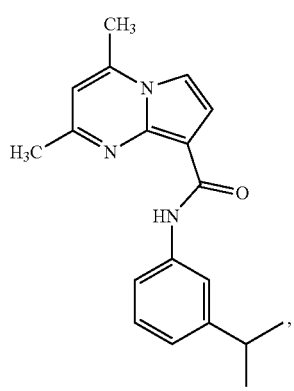
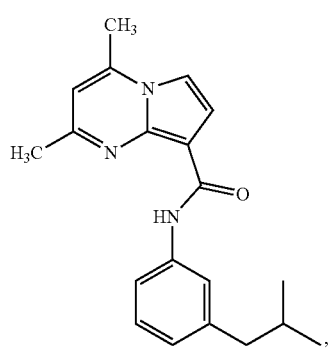
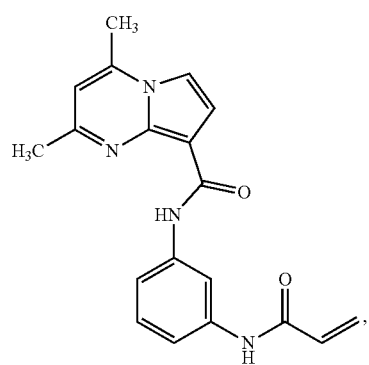
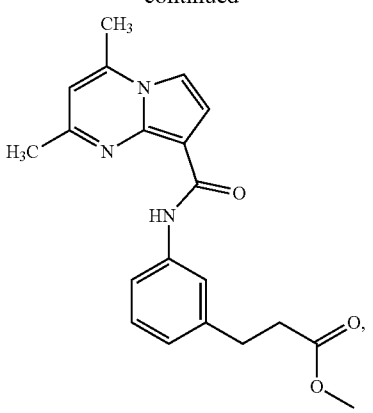
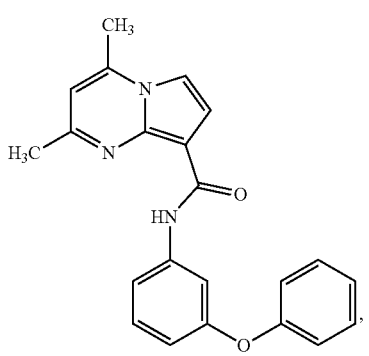
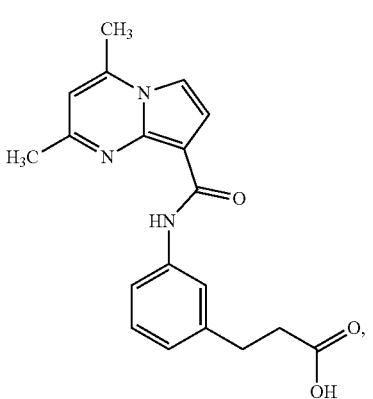
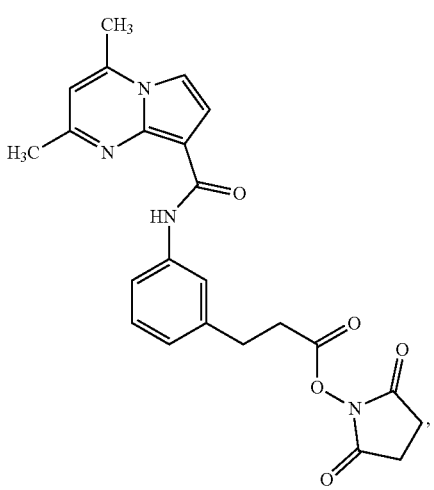

-continued

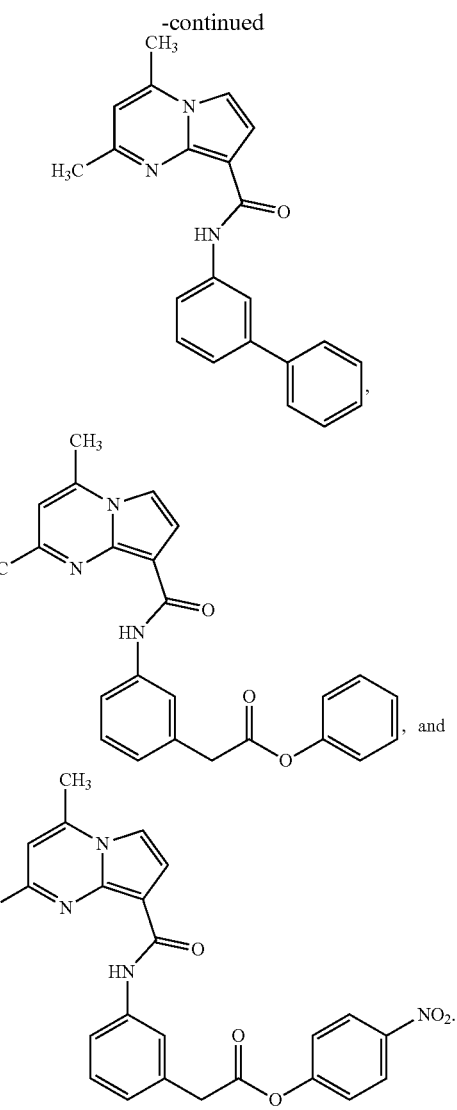

12. A pharmaceutical composition comprising an effective amount of the compound of claim 10 and a pharmaceutical carrier.

13. A method for treating Gaucher's disease or Parkinson's disease in a subject in need thereof, the method comprising administering to the subject the composition of claim 12.

14. A conjugate comprising the compound of claim 12 covalently attached to glucocerebrosidase.

15. A compound or a pharmaceutically acceptable salt thereof having a Formula I:

wherein:

$R^1$ is n is 0-6;

$R^3$ is —N—C(O)—$R^{13}$; and $R^{13}$ is selected from hydrogen, C1-C6 alkyl, C1-C6 (halo) alkyl, and C2-C6 alkenyl.

16. The compound of claim 15 having a formula selected from:

17. A pharmaceutical composition comprising an effective amount of the compound of claim 15 and a pharmaceutical carrier.

18. A method for treating Gaucher's disease or Parkinson's disease in a subject in need thereof, the method comprising administering to the subject the composition of claim 15.

19. A conjugate comprising the compound of claim 15 covalently attached to glucocerebrosidase.

* * * * *